United States Patent
Bryant et al.

(10) Patent No.: US 6,440,362 B1
(45) Date of Patent: Aug. 27, 2002

(54) INTERCONNECTABLE FUMIGANT

(75) Inventors: Harry E. Bryant; Robert R. Emmrich, both of Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/484,141

(22) Filed: Jan. 18, 2000

(51) Int. Cl.⁷ .................................................. A61L 9/00
(52) U.S. Cl. ........................ 422/4; 422/5; 422/122; 422/126; 431/296
(58) Field of Search ............................... 422/126, 122, 422/4, 5; 431/296

(56) References Cited

U.S. PATENT DOCUMENTS

| | | |
|---|---|---|
| 593,990 A | 11/1897 | Deming |
| 1,973,958 A * | 9/1934 | Jones |
| 2,224,622 A | 12/1940 | Waples |
| 2,324,723 A | 7/1943 | Powers et al. .............. 67/22 |
| 2,700,011 A | 1/1955 | Taylor |
| 2,765,579 A | 10/1956 | Gordon |
| 2,770,854 A * | 11/1956 | Miszeika |
| 2,918,750 A | 12/1959 | Blatt |
| 3,754,861 A | 8/1973 | Sadahiro |
| 4,099,916 A | 7/1978 | Gardner et al. ............. 21/116 |
| 4,334,853 A * | 6/1982 | Gardner ........................... 431/2 |
| 4,347,217 A * | 8/1982 | Radkins et al. ............. 422/126 |
| 4,515,768 A | 5/1985 | Hennart et al. |
| 4,600,146 A | 7/1986 | Ohno |
| 4,839,144 A | 6/1989 | Martin |
| 4,849,181 A * | 7/1989 | Kelley et al. .............. 422/109 |
| 4,938,144 A | 7/1990 | Demarest |
| 4,959,925 A | 10/1990 | Nelson et al. |
| 5,447,713 A | 9/1995 | Elsner et al. |
| 5,657,574 A | 8/1997 | Kandathil et al. |
| 5,807,539 A | 9/1998 | Tsukii et al. |
| 5,879,694 A | 3/1999 | Morrison et al. |
| 5,932,204 A | 8/1999 | Joshi |

FOREIGN PATENT DOCUMENTS

EP          0018839          11/1980

OTHER PUBLICATIONS

M. Ansari et al., Field Trial Of Esbiothrin–Impregnated Rope In Ramgarh Village, Dadri PHC, District Ghaziaad (U.P.); Indian Journal Of Malariology; vol. 31, 1994; pp. 57–64.

M. Ansari et al., Esbiothrin–Impregnated Ropes As Mosquito Repellent; Indian Journal Of Malariology; vol. 29; 1992; pp. 203–210.

V. Sharma et al., Insecticide Impregnated Ropes As Mosquito Repellent; Indian Journal Of Malariology; vol. 26; 1989; pp. 179–185.

* cited by examiner

Primary Examiner—Krisanne Thornton

(57) ABSTRACT

An interconnectable fumigant element connectable with like elements to form a segmented fumigant. The fumigant element has a burnable, elongated body holding a volatilizable active. The body has a first connector at one end and a second connector at a location remote from the first connector, the shapes of the first and second connectors being such that a user can use them to connect two such bodies. A second body so connected to a first body is automatically ignited as the first body burns down to its first connector. Two or more such bodies can be connected to form a segmented fumigant. A method of controlling insects by using such fumigant elements is also disclosed, as well as a kit including such fumigant elements for forming burnable and segmented fumigants. The connected fumigants can be stacked in a vertical manner or disposed horizontally.

13 Claims, 2 Drawing Sheets

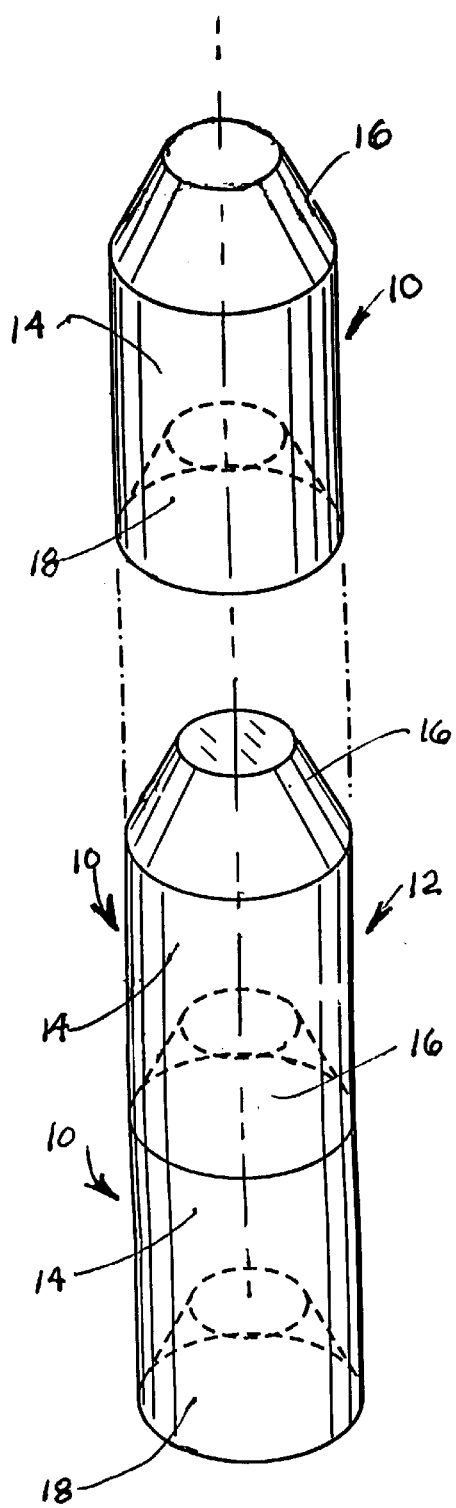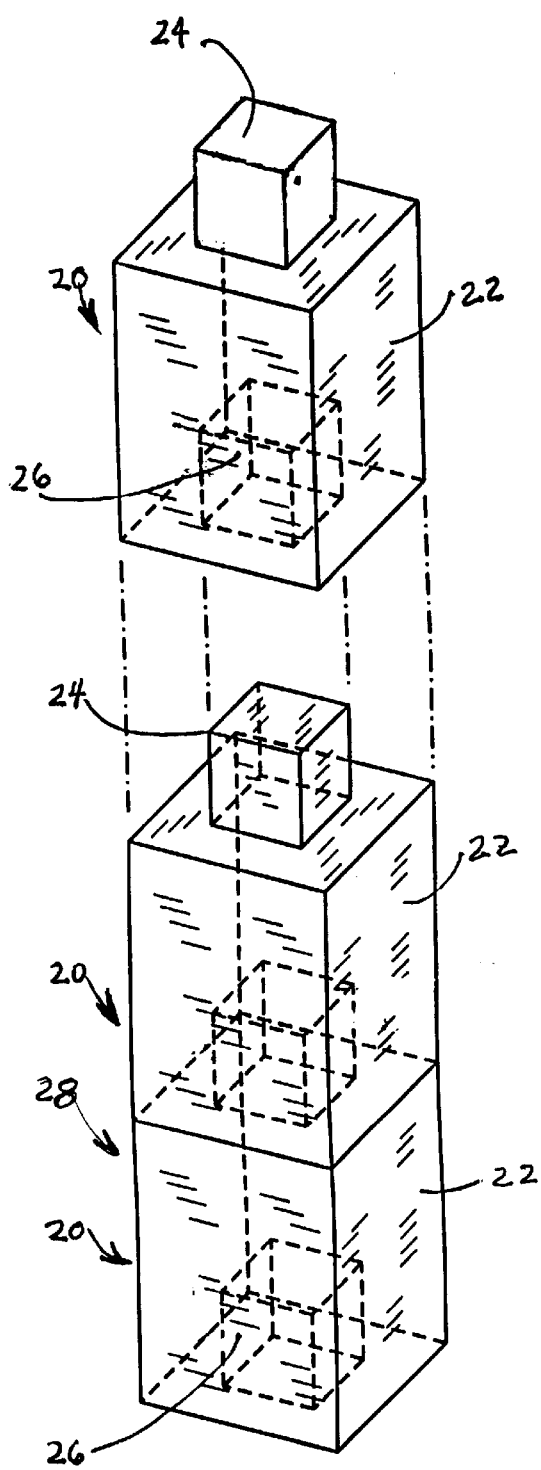
FIG. 1
FIG. 2

INTERCONNECTABLE FUMIGANT

CROSS REFERENCES TO RELATED APPLICATIONS

Not applicable.

STATEMENT REGARDING FEDERALLY SPONSORED RESEARCH

Not applicable.

BACKGROUND OF THE INVENTION

The present invention relates to fumigant structures that are ignited to dispense desired volatile actives.

The term "fumigant" herein means a burnable material that releases a volatile ingredient as the material burns, and preferably as it slowly smolders. A "volatile material" or "volatile ingredient," in that context, burning fumigant including, by way of example only, fragrances, disinfectants, and insect control actives. The term "active" refers to a volatile material to be released in order to achieve the desired effect of the fumigant. For a fumigant intended to repel mosquitoes, for example, an insect repellant would be an "active." An "insect control active" or "insect control ingredient" is an active that repels, kills, or desirably modifies the behavior of insects. "Insects" herein means actual insects, as well as other small animals commonly controlled in conjunction with insects, such as spiders and the like.

The fact that a combustible material may be ignited, so as to then disperse an active, vaporizable ingredient as it continues to smolder, is well known. Incense sticks and mosquito coils are examples of such structures. See e.g. U.S. Pat. Nos. 4,959,925 and 5,657,574. The disclosure of these publications and of all other publications referred to herein are incorporated by reference as if fully set forth herein.

While these types of fumigants are fairly inexpensive, they must be used in considerable numbers over the period of a month, for example, if they are a person's primary means of controlling mosquitoes in sleeping rooms or other living areas, as is common in many parts of the world. One fumigant per night becomes a significant cost for users, especially because these devices are most often used in countries in which annual income levels are very low. In order to make such products widely available in those markets, they must be as inexpensive as possible. In some areas, affordable availability of this type of insect control is particularly important in controlling the spread of malaria and other insect-transmitted diseases.

Traditional, folk remedy approaches to mosquito control include burning widely available, very inexpensive, smoke-producing materials that are used without any insecticide. However, efforts to control mosquitoes by burning materials of this type, such as cow dung or moist leaves, are not very effective and can have other undesirable characteristics, such as excessive odor.

It has also been proposed to use jute rope that has been impregnated with a mosquito repellant as a fumigant. See M. Ansari et al., 31 Indian J. Malariology 57–64 (1994); M. Ansari et al., 29 Indian J. Malariology 203–210 (1992); and V. Sharma et al., 26 Indian J. Malariology 179–185 (1989). This approach shows some promise. However, as with conventional mosquito coils, if the full length of the rope is not needed at a given time, a user must either extinguish the rope or cut it up into smaller lengths. It is common, for example, to burn a fumigant only for the beginning hours of a night. This can require that a user get up in the middle of the night to extinguish a full, normal-sized fumigant so as to reduce the cost of its use.

Thus, there is still a need for improved fumigants, particularly ones that can provide a user with the ability to meter the duration of treatment.

SUMMARY OF THE INVENTION

In one aspect, the invention provides a fumigant element that includes a burnable, elongated body that holds an active to be volatilized by burning of the fumigant element. The body has a first connector at one end and a second connector at a location remote from the first connector. The shapes of the first and second connectors are such that a user can connect or join the first connector of a first body with the second connector of a second body in touching relation such that, when one of the bodies is ignited, the other body will be automatically ignited as the first ignited body burns down to the point at which the two bodies are connected. Various connections between the bodies are possible. By way of example only, these include tongue and groove, tapered projection/tapered recess, and log cabin-type horizontal linkages. Preferably the body is rigid and, also preferably, it is made of compacted plant material. By way of example only, compacted wood powder is a suitable compacted plant material. Most preferably, at least one of the first and second connectors is treated with an igniter material.

A user can assemble a segmented but functionally continuous fumigant by joining or connecting successively as many of the fumigant elements as are necessary to create a segmented fumigant (as discussed, below) that will burn for the desired length of time. For a given use period, a user can join one, two, or more of such bodies for use, thereby adjusting the length of the time over which active is released, as well as its total amount, optimizing fumigant usage and controlling cost.

In a preferred embodiment suitable for controlling insects, the active to be volatilized is an insect control active, preferably selected from among pyrethrum, one or more pyrethroids, and combinations thereof.

As already mentioned, the fumigant elements can be assembled into a segmented fumigant. In another aspect, then, the invention provides a segmented fumigant that includes at least first and second burnable, elongated bodies. Each body holds an active to be volatilized by burning of the body, and each body has a first connector at one end and a second connector at a location remote from the first connector. The first connector of a first one of the bodies is so connected in touching relation to the second connector of a second body that the second body is automatically ignited as the first body burns from a location that is remote from its point of connection to the second body to the end of the first body at which it is connected to the second body. Preferably at least one of the connected first and second connectors of the first and second bodies is treated with an igniter material, which aids in the smooth transfer of burning from the first to the second body.

Preferably, the first and second connectors of successive, connected, individual fumigant elements are frictionally engaged or mechanically interlocked. More preferably, they are frictionally engaged, mechanically interlocked, or otherwise so engaged so securely that, when the segmented fumigant is resting on a supporting surface, the first and second bodies (and any additional attached bodies) are sufficiently engaged that the segmented fumigant remains intact when in a position convenient for burning, without requiring external support above the supporting surface.

In an alternative embodiment of the segmented fumigant of the invention, the active of the first body is different from the active of the second body. By that means, a single, segmented fumigant can deliver two or more actives in succession. When the actives are fragrances, for example, successive, different fragrances can be delivered. Without limitation, a second body entirely free of an active also will be understood as having an active different from the active of the first body, making possible, by way of example only, the delivery of bursts of active, separated in time.

The invention further provides a method of dispensing volatile actives that includes the following steps. The first step is to provide at least two fumigant elements, as described above, each fumigant element including a burnable, elongated body holding an active to be volatilized by burning of the fumigant element, the body having a first connector at one end and a second connector at a location remote from the first connector, the shapes of the first and second connectors being such that a user can connect the first connector of a first body with the second connector of a second body in touching relation such that the second body will be automatically ignited as the first body burns down to its first connector.

Then the first connector of a first fumigant element is connected to the second connector of a second fumigant element to join the two fumigant elements. Then one of the connected fumigant elements is ignited at a location distant from its point of connection with the other fumigant element and is allowed to burn. The steps of connecting and igniting can be performed in reverse order, at the preference of any given user. The fumigant elements can be assembled into many different possible geometric arrays. In a preferred arrangement, the fumigant elements are vertically stacked, one on top of the other.

In a preferred embodiment of the method of the invention, the active held by at least one of the fumigant elements provided in the first step, above, is an insect control active, although fragrances or any other active may be used in addition to or instead of an insect control active. In another embodiment, at least two fumigant elements hold differing actives. A preferred base material for forming the bodies is compacted sawdust, as an example of compacted plant material. In one especially preferred form, at least one end of one of the bodies is treated with an igniter material, such as an alkali metal nitrate, sodium or potassium nitrate being preferred. The igniter material can facilitate lighting a first body and also ensure a smooth burning transition between successive bodies in a multi-body fumigant. Various connections between the bodies are possible. By way of example only, these include tongue and groove, tenon and mortise, tapered projection/tapered recess, and log cabin-type horizontal linkages.

In another aspect, the invention provides a kit for forming a burnable fumigant. The kit includes a first compact mass of material in the form of an elongated first body having a first connector. There is also a second compact mass of material in the form of an elongated second body having a second connector. A volatilizable active is held by the first and second bodies, whether on a surface of, impregnated in, or otherwise borne by the bodies. Preferred actives are insect control ingredients and fragrances. When the first connector of the first body is connected to the second connector of the second body, a segmented but functionally continuous fumigant is formed. In some preferred forms, the elongated bodies are between 3 and 10 cm in length. A preferred width of the bodies is between 5 mm and 15 mm.

A wide variety of actives are suitable for use with the present invention. Pyrethrum and pyrethroid type materials commonly now used in mosquito coils are likely to be most useful. Preferred pyrethroids (from the standpoint of expense, activity, or both vis a vis mosquitoes) are d-allethrin, allethrin, prallethrin, bioallethrin, s-bioallethrin, esbiol, dichlorvos, transfluthrin, pyrethrum, and combinations thereof. Other insect control ingredients can also be used, such as the repellents DEET, citronella, lemon grass oil, lavender oil, cinnamon oil, neem oil, clove oil, sandalwood oil, and geraniol, and the insect growth regulators such as hydroprene.

Volatilizable fragrances, such as those typically used in incense sticks, can be used instead of or in addition to an insect control active. A wide variety of such volatile fragrances are well known to those skilled in the art.

These and still other features and advantages of the present invention will be apparent from the description of the preferred embodiments which follows. The following embodiments are merely preferred embodiments. The claims should be looked to in order to judge the full scope of the invention.

BRIEF DESCRIPTION OF THE DRAWINGS

FIG. 1 is a partially exploded perspective view of a first embodiment of the segmented fumigant of the invention assembled from fumigant elements of the invention.

FIG. 2 is a view similar to FIG. 1, but of a second embodiment of the segmented fumigant of the invention.

DETAILED DESCRIPTION

Figure 3:
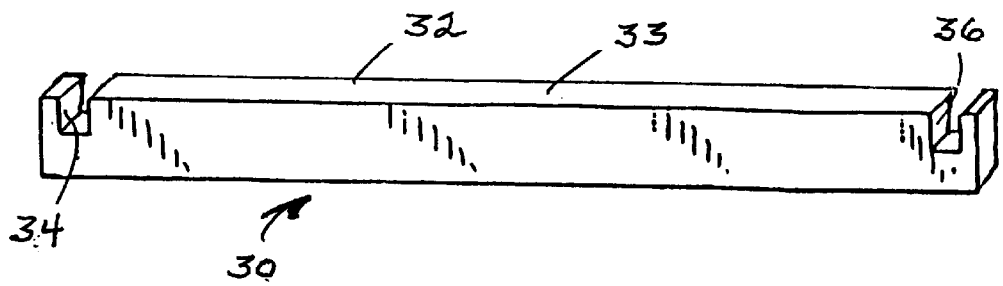
FIG. 3 is a side perspective view of a third embodiment of a fumigant element of the invention.

Turning now to the drawings, wherein like reference numbers refer to like and corresponding parts throughout the several views, FIG. 1 shows a fumigant element of the invention, shown generally at 10, combined with identical second and third fumigant elements to show, in a partially exploded perspective view, a segmented fumigant of the invention (shown generally at 12).

The fumigant element 10 has a burnable, elongated body 14 that, preferably, is rigid and made of compacted wood powder, sawdust, or other suitable plant materials such as peanut or soybean shells. The body 14 is capable of holding an active to be volatilized when the body is burned. The body 14 has a first connector 16 at one end, the first connector in the embodiment shown at 10 being in the form of a truncated, endwardly extending cone. The body 14 also has a second connector 18 (shown in phantom in FIG. 1) situated at a location remote from the first connector 16, in the fumigant element 10, being located at the end of the body 14 opposite to the location of the first connector. The second connector 18 of the embodiment shown at 10 is a cone-shaped cavity of substantially the same size and shape as the cone-shaped first connector 16. Alternative locations, sizes, and shapes of the first and second connectors will be apparent to those skilled in the art.

The shapes of the first and second connectors 16,18 are such that a user can join the first connector 16 of a first body 14 with the second connector 18 of a second body 14 in intimately attached relation, with the two bodies in touching contact with each other. Consequently, when one of the bodies is ignited and burns down to its point of contact with the other body, the other body will be automatically ignited and continue to burn. Preferably, at least one of the first and second connectors of each body is treated with an igniter material to facilitate the ignition of an additional body connected to it. Preferred igniter materials are alkali metal nitrates, sodium or potassium nitrate being preferred. When multiple bodies 14 are vertically stacked, successive bodies are so joined as to be sufficiently mechanically engaged that the resulting segmented fumigant (shown generally at 12 in FIG. 1) remains intact, in a position convenient for burning, without requiring external support above the supporting surface on which it rests.

Various shapes of burnable bodies are possible and will be apparent to those skilled in the art, along with various shapes and locations of first and second connectors. Thus, while the fumigant element 10 is shown with a basically cylindrical shape and cone-shaped first and second connectors, FIG. 2 shows an embodiment of the invention having fumigant elements (shown generally at 20) that have longitudinally extended bodies 22 having generally square lateral cross-sectional shapes. The box-like bodies 22 are shown having first and second connectors 24,26 in the shape of rectangular tenons and mortises, respectively (second connector 26 being shown in phantom). This arrangement has the advantage that, when first and second bodies 22 of first and second fumigant elements 20 are joined by inserting the tenon-shaped first connector 24 of the first body into the mortise-shaped second connector of the second body and then placed on a fire-proof supporting surface (not shown), the first and second bodies are so joined as to be sufficiently mechanically engaged that the resulting segmented fumigant (shown generally at 28 in FIG. 2) remains intact, in a position convenient for burning, without requiring external support above the supporting surface on which it rests.

Figure 4:
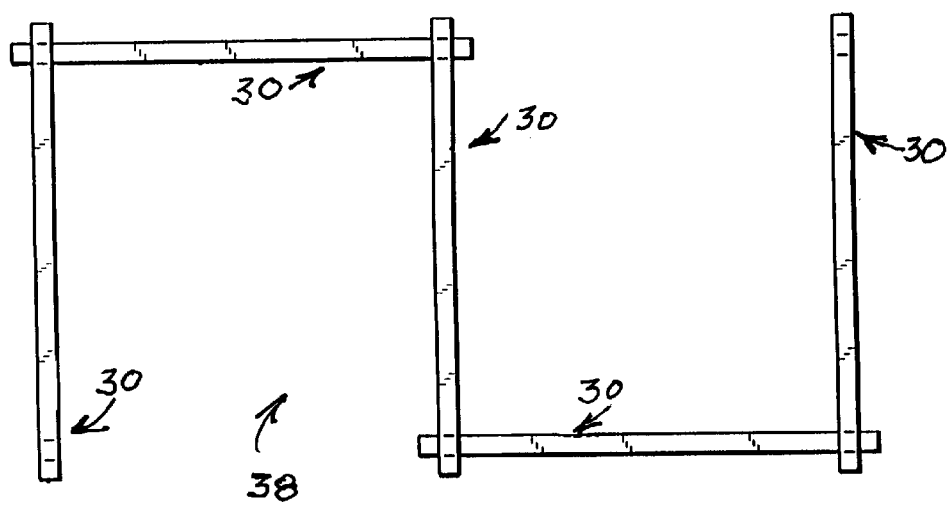
FIG. 4 is a top plan view of multiple FIG. 3 fumigant elements that are interlocked to form an additional embodiment of the segmented fumigant of the invention.

A third embodiment of the fumigant element of the invention is shown generally at 30 in FIGS. 3 and 4. In this embodiment, the fumigant element 30 has an extended body 32 that is rectangular in cross section so as to have a surface extending the length of the body, here arbitrarily designated the upper surface 33, other cross sectional shapes being apparent to one skilled in the art. First and second connectors 34,36 are located at the opposite ends of the body 32. The first and second connectors 34,36 both have the same shape, namely a straight slot extending transversely across the body 32, both in the upper surface 33. Two or more fumigant elements 30 can be linked by fitting together the first and second connectors 34,36 of successive fumigant elements in facing relation. By this means, a segmented fumigant can be formed, as shown generally in FIG. 4 at 38.

With all of the embodiments of the fumigant elements shown (as well as alternative shapes that will be apparent to those skilled in the art), as many fumigant elements can be connected as is desired, creating a segmented fumigant of a desired length and burning time. Furthermore, connectable fumigant elements can be made differing in length, cross-sectional size, density or other characteristics that affect burning time, and different fumigant elements can be loaded with different actives. These differing fumigant elements then can be assembled at the discretion of the use to adjust burning time as well as the selected successive delivery of different actives.

When delivery of an insect control active is desired, a preferred formulation for the bodies which make up the fumigant elements is as follows:

| Ingredient | Function | Wt. % |
|---|---|---|
| sawdust, 100 mesh | filler for combustion | 85.50 |
| d-allethrin - sawdust mix, 10% active | insect control active | 4.00 |
| Avicel PH-102/microcrystalline cellulose (available from FMC Corp.) | dry press molding agent | 10.00 |
| potassium nitrate | burn rate enhancer | 0.50 |

The first three ingredients can be mixed together. The resulting mass is fed into a conventional compression die machine (such as a Stokes press), where the mass is compressed between two dies. Suitable dies are selected to create a fumigant element of the desired shape. The amount of compression applied to the ingredients can vary the burning time.

The potassium nitrate is then applied to one or both of the first and second connectors of the fumigant elements, preferably by simply spraying or otherwise treating the connectors with a potassium nitrate solution and allowing the solution to dry.

Another suitable formula is as follows. The first five ingredients are mixed with mild heating until a paste is formed. Then the next six ingredients are added to the paste until a uniform dough is formed. The resultant dough is extruded in the desired cross-sectional shape.

| Ingredient | Function | Wt. % |
|---|---|---|
| water | solvent | 47.000 |
| corn starch | binder | 10.600 |
| sodium benzoate | preservative | 0.159 |
| malachite green dye | provide color | 0.133 |
| potassium nitrate | burn rate enhancer | 0.530 |
| kerosene | solvent | 1.590 |
| d,1 allethrolone d-trans chrysanthemate | insect control active | 0.030 |
| wood powder | filler for combustion | 35.877 |
| charcoal | combustion aid | 3.180 |
| guar gum | lubricant | 0.636 |
| talc | provides aesthetic white ash | 0.265 |

Yet another suitable formula is as follows:

| Ingredient | Function | Wt. % |
|---|---|---|
| Corn starch | binder | 14.6% |
| Potassium nitrate | burn rate modifier | 0.73% |
| Water | solvent | 70.1% |
| Wood powder (100 mesh) | filler for combustion | 14.6% |

The first three ingredients are mixed with mild heating until a paste is formed. Then the wood powder is mixed in until a uniform dough is formed. The resultant dough is extruded in the desired cross-sectional shape. For example, a cylindrical shape can be extruded, preferably from 10 to 14 mm in diameter, cut to form fumigant elements of a desired length in an operation that forms the first and second connectors, and allowed to dry. An igniter material can be added by dipping or otherwise treating the first and second connectors. It is convenient and preferred to cut fumigant elements to the length needed to burn one hour, allowing a user to easily estimate how many fumigant elements to join to create a segmented fumigant that will burn for the number of hours desired. An active ingredient such as an insecticide, repellent, or fragrance can be added to the dough mixture prior to extrusion. Alternatively, and with certain handling and manufacturing advantages, the active can be applied by coating, dipping, spraying, or other means after the fumigant element has dried.

The preceding description is merely of preferred embodiments of the invention. One skilled in the art will readily apprehend alternative embodiments that nevertheless fall within the scope and breadth of the invention. Thus, the claims should be looked to in order to understand the full scope of the invention.

Industrial Applicability

The invention provides devices for dispensing volatile materials for preselected durations.

What is claimed is:

1. A segmented fumigant comprising at least first and second burnable, elongated bodies, each body holding an active to be volatilized by burning of the body, and each body having a first connector at one end and a second connector at a location remote from the first connector, the first connector of one of the bodies being interconnected in touching relation to the second connector of the other body such that the second body is automatically ignited as the first body burns from a location that is remote from its point of interconnection to the second body to the location on the first body at which it is interconnected to the second body;

wherein at least one of the first and second connectors is treated with a burn rate modifying igniter material adjacent where the first connector of one of the bodies is interconnected to the second connector of the other body.

2. The segmented fumigant of claim 1 wherein, when the fumigant is resting on a supporting surface, the first and second bodies are so interconnected and vertically stacked as to be sufficiently mechanically engaged that the segmented fumigant remains intact when oriented in an essentially vertical position convenient for burning, without requiring external support above the supporting surface from anything other than the fumigant.

3. The segmented fumigant of claim 1 wherein the igniter material is selected from the group consisting of alkali metal nitrates.

4. The segmented fumigant of claim 1 wherein the active of the first body is different from the active of the second body.

5. The segmented fumigant of claim 4 wherein the actives are fragrances.

6. A method of dispensing volatile actives comprising the steps of:

a. providing at least two fumigant elements, each fumigant element including a burnable, elongated body holding an active to be volatilized by burning of the fumigant element, the body having a first connector at one end and a second connector at a location remote from the first connector, the shapes of the first and second connectors being such that a user can join the first connector of a first body with the second connector of a second body in touching interconnected relation such that the second body will be automatically ignited as the first body burns down to its first connector;

b. assembling the first connector of a first fumigant element to the second connector of a second fumigant element to form a self-supporting interconnected assembly consisting of the two fumigant elements; and c. igniting one of the joined fumigant elements, of the self-supporting interconnected assembly consisting of the two fumigant elements, at a location distant from its point of interconnection with the other fumigant element.

7. The method of claim 6, wherein the active held by at least one of the fumigant elements is an insect control active.

8. The method of claim 6, wherein at least two fumigant elements hold differing actives.

9. A kit for forming a burnable fumigant, comprising:

a first compact mass of material in the form of an elongated first body having a first connector;

a second compact mass of material in the form of an elongated second body having a second connector, the shapes of the first and second connectors being such that a user can interconnect the first connector of the first body with the second connector of the second body in touching interconnected relation; and a volatilizable active held on the first and second bodies, wherein the active is selected from the group consisting of insect control actives and fragrances;

the first and second bodies being so configured that, when the first connector is joined with the second connector in interconnected fashion, one of the thereby attached bodies can be lit so as to burn that body as well as thereafter causing at least a portion of the other body to burn;

wherein at least one of the first and second connectors is treated with a burn rate modifying igniter material.

10. The kit of claim 9, wherein the bodies may be vertically stacked one on top of the other to form the fumigant.

11. The kit of claim 9, wherein the first and second bodies are of different lengths from each other.

12. The kit of claim 9, wherein the igniter material is selected from the group consisting of alkali metal nitrates.

13. The kit of claim 9, wherein the second connector is a tapered cavity and the first connector is a tapered projection.

* * * * *